United States Patent [19]
Johansen

[11] Patent Number: 5,513,650
[45] Date of Patent: May 7, 1996

[54] GUIDEWIRE EXTENSION CONNECTOR - KEYED JOINT

[75] Inventor: Jerald A. Johansen, Canyon Lake, Calif.

[73] Assignee: Medtronic, Inc., Minneapolis, Minn.

[21] Appl. No.: 396,043

[22] Filed: Feb. 28, 1995

[51] Int. Cl.⁶ .................................................. A61B 5/00
[52] U.S. Cl. .................................................. 128/772
[58] Field of Search ...................... 128/657, 658, 128/772; 604/95, 280–283; 403/292, 298, DIG. 4

[56] References Cited

U.S. PATENT DOCUMENTS

| | | | |
|---|---|---|---|
| 4,827,941 | 5/1989 | Taylor et al. | 128/657 |
| 4,917,103 | 4/1990 | Gambale et al. | 128/772 |
| 4,922,923 | 5/1990 | Gambale et al. | 128/772 |
| 4,966,163 | 10/1990 | Kraus et al. | 128/772 |
| 5,031,636 | 7/1991 | Gambale et al. | 128/772 |
| 5,109,867 | 5/1992 | Twyford, Jr. | 128/772 |
| 5,113,872 | 5/1992 | Jahrmarkt et al. | 128/772 |
| 5,188,621 | 2/1993 | Samson | 604/283 |
| 5,191,888 | 3/1993 | Palmer et al. | 128/657 |
| 5,195,535 | 3/1993 | Shank | 128/772 |
| 5,197,486 | 3/1993 | Frassica | 128/772 |
| 5,234,002 | 8/1993 | Chan | 128/772 |
| 5,267,573 | 12/1993 | Evans et al. | 128/772 |
| 5,271,415 | 12/1993 | Foerster et al. | 128/772 |
| 5,275,173 | 1/1994 | Samson et al. | 128/772 |

*Primary Examiner*—Max Hindenburg
*Attorney, Agent, or Firm*—Michael R. Shevlin; Dianne M. F. Plunkett; Harold R. Patton

[57] ABSTRACT

A guidewire extension assembly for use in angioplasty to facilitate exchanging a balloon dilitation catheter that includes a guidewire and an extension wire that are releasably connected thus avoiding the need to use a separated exchange wire. The proximal end of the guidewire and the distal end of the extension wire either have one or more slots or one or more keys and when joined together cream a guidewire extension system utilizing a keyed joint connection. The key, when inserted in the slot, is held in place by frictional engagement to connect the distal end of the extension wire to the proximal end of the guidewire. The keyed connection between the guidewire and the extension wire makes it simple to attach the wires together, transfers torsional forces between the wires without the fear of the wires coming apart or unscrewing and is readily disconnected/reconnected when required.

19 Claims, 1 Drawing Sheet

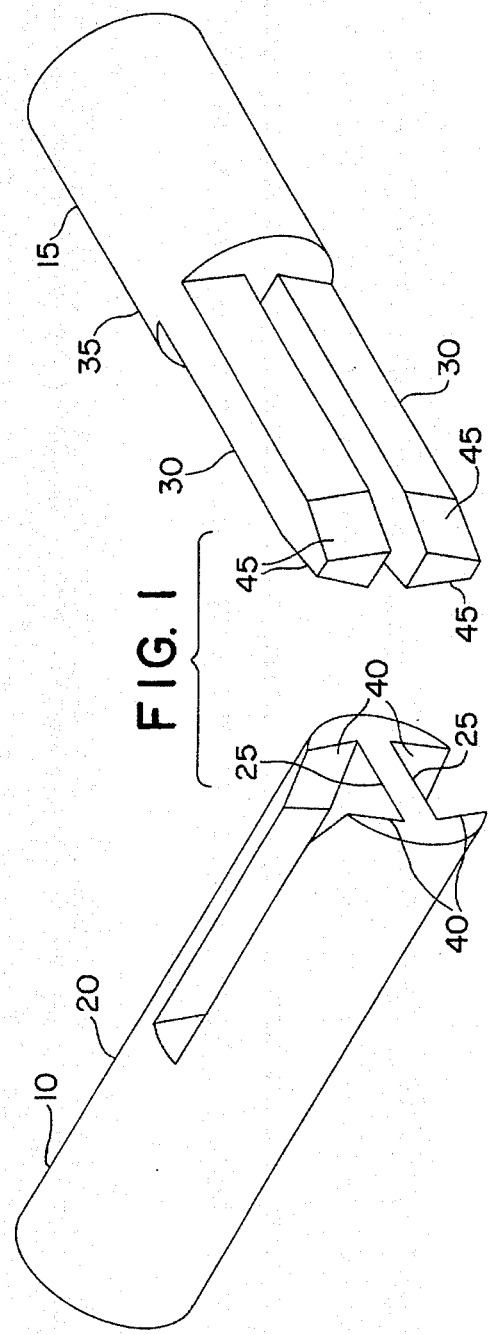
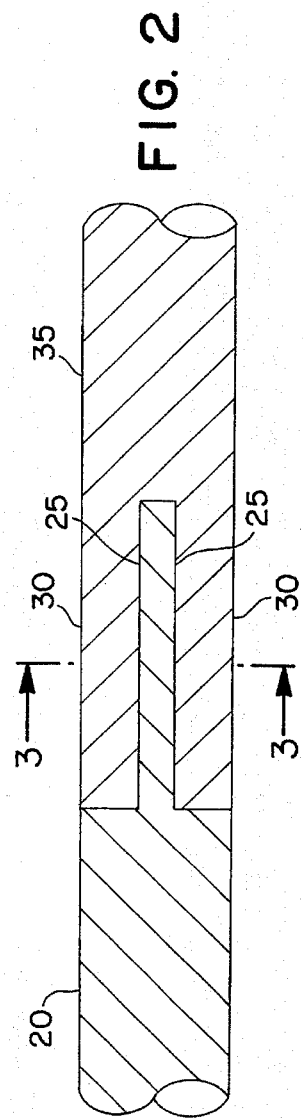
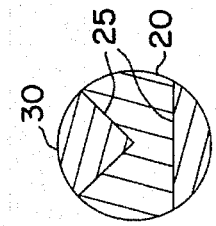
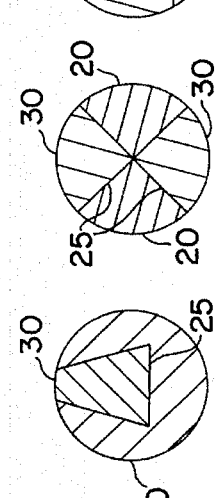
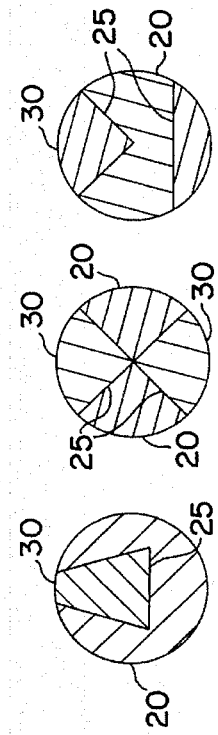
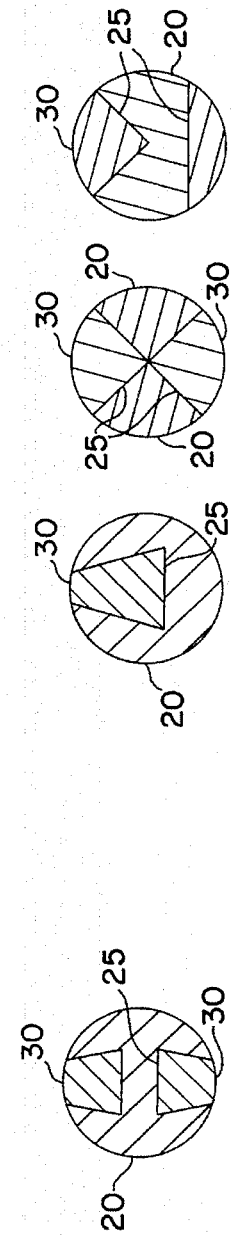

GUIDEWIRE EXTENSION CONNECTOR - KEYED JOINT

FIELD OF THE INVENTION

This invention relates to guidewires used in angioplasty, and more particularly to the extension of the guidewire to facilitate the exchange of dilatation catheters

BACKGROUND OF THE INVENTION

Dilatation balloon catheters are frequently used for the treatment of stenosis in the coronary arteries. This procedure, known as percutaneous transluminal coronary angioplasty (PCTA), was developed by Dr. Andreas Gruntzig. According to this procedure, blockage in a coronary artery can be reduced by positioning a balloon dilatation catheter across the blockage and inflating the balloon, which causes stretching of the artery and pressing of the lesion into the artery wall to re-establish acceptable blood flow through the artery. The first marketable PCTA catheters for angioplasty were "fixed wire" catheters, in which a core or guidewire was fixed within the catheter to stiffen it so that it could be pushed into position in the vascular system. If a different catheter size was required, the fixed wire catheter had to be completely removed and a new one inserted. This is a tedious and time consuming process.

Dr. John Simpson and Dr. Edward Robert subsequently developed an "over-the-wire" catheter in which a guidewire was slidably placed within a lumen of the catheter. The guidewire lumen passed from the distal end of the catheter through the balloon to the proximal end of the catheter. This system provided reasonably easy placement of the catheter because the guidewire was inherently smaller and more flexible than the fixed wire system so one could more readily select the desired coronary artery and reach smaller branches. Once the guidewire was positioned beyond the stenosis, the catheter was then slid over the guidewire so that placement of the balloon spanned the stenosis and the balloon was then inflated. Once the catheter has been inflated to dilate the stenosis, it is not uncommon for the physician to require use of a subsequent larger size of catheter to open the artery. There are different methods used to exchange the catheter and all of them have the same goal, to exchange the catheter without losing the position across the stenosis.

When performing the catheter exchange it is important to keep the guidewire in the same position so that the guidewire may be used to guide the next catheter to the stenosis. The most common method of exchange is to remove the initial guidewire and replace it with an exchange wire that is over double the length of the catheter. Once the exchange wire is in place, the catheter is slid over the exchange wire and the catheter is removed, then the next catheter is slid over the exchange wire to the stenosis. This procedure is time consuming and awkward.

Another method of exchanging the catheter is to use an extension wire. The extension wire is attached to the proximal end of the guidewire that is already in place. With the extension wire attached, the combination of the guidewire and extension wire is approximately the same length as an exchange wire. The advantage of this method is that the original guidewire that has already crossed the stenosis does not have to be disturbed during the catheter exchange.

There are different methods of attaching the extension wire to the guidewire. U.S. Pat. No. 4,917,103 to Gambale describes a male/female connection between the guidewire and extension wire that crimps the extension wire to the proximal end of the guidewire making a permanent connection. U.S. Pat. No. 5,197,486 to Frassica describes a connection where the proximal end of the guidewire has a reduced diameter male element that attaches to a female element at the distal end of the extension wire by using a interference fit. U.S. Pat. No. Re. 34,366 to Taylor describes another male/female connection between the guidewire and the extension wire.

There are other methods that add intermediate parts between the guidewire and extension wire that connects them together (see U.S. Pat. No. 5,188,621 to Samson, U.S. Pat. No. 5,271,415 to Foerster, U.S. Pat. No. 5,234,002 to Chan, U.S Pat. No. 4,922,923 to Gambale, U.S. Pat. No. 5,031,636 to Gambale) or use retractable sleeves which enclose interlocking members of the guidewire and extension wire (see U.S. Pat. No. 5,109,867 to Twyford).

There are problems associated with the aforementioned connections. Connections that use male/female friction to hold the wires together may disconnect if any torsional forces are used during the exchange. Connections that use crimping devices require special equipment, may be somewhat awkward to use and are not readily disconnectable. Connections with intermediate parts cannot connect the wires if those parts are lost or misplaced during a procedure. Connections using retractable sleeves may jam or stick with foreign material and not allow the connection.

The object of the invention is to provide a new and improved guidewire extension that cures the problems that have been encountered by prior extension systems. This is accomplished by making a connection between the guidewire and the extension wire that makes it simple to attach the wires together, can transfer torsional forces between the wires without the fear of the wires coming apart or unscrewing and can be readily disconnected/reconnected when required.

SUMMARY OF THE INVENTION

Accordingly, the present invention is directed to a guidewire extension utilizing a keyed joint connection between the guidewire and the extension wire, thus avoiding the need for a separate exchange wire when exchanging a balloon dilitation catheter. The proximal end of the guidewire and the distal end of the extension wire either have one or more slots or one or more keys and when joined together create a guidewire extension system utilizing a keyed joint connection. The key, when inserted in the slot, is held in place by frictional engagement to connect the distal end of the extension wire to the proximal end of the guidewire. The keyed connection between the guidewire and the extension wire makes it simple to attach the wires together, transfers torsional forces between the wires without the fear of the wires coming apart or unscrewing and is readily disconnected/reconnected when required.

BRIEF DESCRIPTION OF THE DRAWINGS

The foregoing and other features of the present invention will be best appreciated with reference to the following detailed description of a specific embodiment of the invention, when read in conjunction with the accompanying drawings.

FIG. 1 is an enlarged perspective view of the proximal end of the guidewire and the distal end of the extension wire showing the keyed joint connection features of the invention.

FIG. 2 is an enlarged longitudinal cross-sectional view showing the assembled keyed joint of the guidewire and extension wire assembly of FIG. 1.

FIG. 3 is a transverse cross-sectional view taken at 3—3 of FIG. 2 showing the keyed joint assembled.

FIG. 4 is an additional cross-sectional view showing an alternate configuration for the keyed joint assembly.

FIG. 5 is an additional cross-sectional view showing an alternate configuration for the keyed joint assembly.

FIG. 6 is an additional cross-sectional view showing an alternate configuration for the keyed joint assembly.

DETAILED DESCRIPTION OF THE PREFERRED EMBODIMENTS

The present invention is directed to a guidewire extension utilizing a keyed joint connection between the guidewire and the extension wire, thus avoiding the need for a separate exchange wire when exchanging a balloon dilatation catheter. The proximal end of the guidewire and the distal end of the extension wire either have one or more slots or one or more keys and when joined together create a guidewire extension system utilizing a keyed joint connection. The key, when inserted on the slot, is held in place by frictional engagement to connect the distal end of the extension wire to the proximal end of the guidewire.

FIG. 1 shows the present invention of an extendable guidewire, which includes guidewire 10 with diametrically opposed attachment slots 25 at its proximal end 20 and an extension wire 15 with diametrically opposed keys 30 at its distal end 35.

Guidewire 10 is made of standard guidewire construction modified at its proximal end 20 with attachment slots 25. Standard guidewires for angioplasty are constructed of stainless steel and have a diameter of about 0.014". The exact construction of guidewire 10 (other than the proximal end) is not critical to the invention and will not be described in any detail. Extension wire 15 is generally formed from a elongated, constant diameter wire. The guidewire 10 and extension wire 15 are preferably constructed out of stainless steel and have a diameter of about 0.014".

Details of the connection ends of guidewire 10 and extension wire 15 are shown in FIG. 1. The extension wire 15 is constructed with attachment keys 30 at the distal end 35. The proximal end 20 of guidewire 10 is constructed with attachment slot 25. The guidewire 10 is connected to the extension wire 15 by mating the proximal end 20 of the guidewire 10 and the distal end 35 of the extension wire 15 so that keys 30 engages slots 25, as shown in FIG. 2. Keys 30 are dimensioned to fit inside attachment slots 25 at the proximal end 20 of guidewire 10 with a interference fit. In one embodiment, slots 25 have tapers 40 at the proximal end and keys 30 have tapers 45 at the distal end. Tapers 40 and 45 will make it easy to start the engagement between slots 25 and keys 30. The length of key 30 can vary between 0.050 to 0.500 inches, the height and width can vary between 0.0035 and 0.007 inches, depending on the key 30 configuration. FIG. 3 shows a cross-sectional view of the connection between key 30 and slot 25. The connection between key 30 and slot 25 shall provide interference or frictional fit which will hold guidewire 10 and extension wire 15 together during the catheter exchange and resist disengagement but can be readily disengaged after exchange has been made. Preferably no more than a one pound pull should be necessary for disengagement.

The proximal end 20 of guidewire 10 is adapted to frictionally engage and secure the distal end 35 of extension wire 15 so that rotation of extension wire 15 causes rotation of guidewire 10 through the connection. Extension wire 15 is sufficiently long so that when the guidewire 10 and extension wire 15 are connected together, the combination has an overall length suitable for exchanging catheters without removing guidewire 10 from the patients vascular system. The length of guidewire 10 is approximately 175 cm and the length of extension wire 15 is approximately 125 cm. The connection between the two wires provides a smooth, substantially continuous outer diameter between the guidewire 10 and extension wire 15. The smooth, continuous outer diameter of the connection prevents snagging of the catheter during the exchange.

The shapes and dimensions of both keys 30 and slots 25 can have many configurations. FIG. 4 shows an alternate configuration for key 30 and slot 25. In this configuration, there is only one key 30 to engage slot 25. FIG. 5 shows an alternate configuration where the key 30 and slot 25 are essentially the same size and form an X shape when joined. FIG. 6 shows another alternate where there are two key 30 having different shapes and could be assembled one way. This configuration could be used if the orientation between guidewire 10 and extension wire 15 is important.

In use, guidewire 10 is introduced into the patient with a balloon dilatation catheter in the patients femoral artery. The guidewire 10 is advanced to the selected coronary artery and across the stenosis, as seen in U.S. Pat. No. 4,917,103 to Gambale, which is hereby incorporated by reference. Once in place, guidewire 10 is held in place as the balloon dilitation catheter is advanced along guidewire 10 until the inflatable balloon spans the stenosis. The balloon is then inflated to dilate the stenosis. While in the patient, the only pan of the guidewire 10 that is exposed is the proximal end 20 with slot 25. To exchange the catheter, the balloon is deflated. The distal end 35 of extension wire 15 is then attached to the proximal end of guidewire 10 by sliding key 30 into slot 25 until firmly seated for positive engagement. Once connected, guidewire 10 and extension wire 15 will act as one unit and may be twisted and rotated. While holding the extension wire 15, the balloon catheter is removed by sliding it off over the extension wire 15. The new catheter is then slid on over the extension wire 15 and guidewire 10 until its balloon reaches the stenosis. Extension wire 15 may then be disengaged from guidewire 10 by pulling it apart at the keyed joint.

Although a particular embodiment of the invention has been described herein in some detail, this has been done for the purposes of illustration only and is not intended to be limiting with regard to the scope of the present invention as defined in the claims. It is contemplated that various substitutions, alterations, and/or modifications, including but not limited to those specifically discussed herein, may be made to the embodiment described herein without departing from the spirit and scope of the present invention. For example, guidewire 10 and/or extension 15 could be made of different metals or plastic and the diameter of each could vary.

| No. | Component |
|-----|-----------|
| 10  | Guidewire |
| 15  | Extension Wire |
| 20  | Guidewire - Proximal end |
| 25  | Slot |

| No. | Component |
|---|---|
| 30 | Key |
| 35 | Extension Wire - Distal end |
| 40 | Taper (proximal end of slot 25) |
| 45 | Taper (distal end of key 30) |

What is claimed is:

1. A guidewire extension assembly for angioplasty including a guidewire and an extension wire to facilitate exchanging a balloon dilatation catheter comprising:
   (a) a guidewire having a proximal end and a distal end;
   (b) an extension wire having a proximal end and a distal end;
   (c) the proximal end of the guidewire and the distal end of the extension wire being connectedly matable with each other, the connection between the mating ends including one or more non-circular slots on one mating end, each slot being a recessed chamber open at the mating end, exposed along the exterior extending longitudinally and one or more non-circular keys on the other mating end, each key having dimensions complementary to the slot; and
   (d) the key when inserted in the slot forms a circle and is held in place by frictional engagement to connect the distal end of the extension wire to the proximal end of the guidewire.

2. The guidewire extension assembly of claim 1 wherein the slots are formed in the proximal end of the guidewire and the keys are formed on the distal end of the extension wire.

3. The guidewire extension assembly of claim 1 wherein the slots are formed in the distal end of the extension wire and the keys are formed on the proximal end of the guidewire.

4. The guidewire extension assembly of claim 1 wherein the slot and the key have a taper on the mating ends to facilitate engagement.

5. The guidewire extension assembly of claim 1 wherein the guidewire and extension wire are made of stainless steel.

6. The guidewire extension assembly of claim 1 wherein the guidewire and extension wire are made of plastic.

7. The guidewire extension assembly of claim 1 wherein the guidewire and extension wire have a diameter of about 0.014 inches.

8. A guidewire extension assembly for angioplasty including a guidewire and an extension wire to facilitate exchanging a balloon dilatation catheter comprising:
   (a) a guidewire having a proximal and distal end, the proximal end having one or more non-circular attachment slots, each slot being a recessed chamber open at the mating end, exposed along the exterior extending longitudinally;
   (b) an extension wire having a proximal and distal end, the distal end having one or more non-circular keys, each key having dimensions complementary to the slot;
   (c) the key and slot being dimensioned for an interference fit with firm but releasably connectable engagement, the combination of slot and key forming a circle; and
   (d) the proximal end of the guidewire and the distal end of the extension wire being connectedly joined and unjoined with each other using the key and attachment slot.

9. The guidewire extension assembly of claim 8 wherein the slot and the key have a taper on the mating ends to facilitate engagement.

10. The guidewire extension assembly of claim 8 wherein the guidewire and extension wire are made of stainless steel.

11. The guidewire extension assembly of claim 8 wherein the guidewire and extension wire are made of plastic.

12. The guidewire extension assembly of claim 8 wherein the guidewire and extension wire have a diameter of about 0.014 inches.

13. A method used in angioplasty for connecting an extension wire to a guidewire comprising the steps of:
   (a) providing a guidewire section having proximal and distal ends, the proximal end having one or more non-circular attachment slots, each slot being a recessed chamber open at the mating end, exposed along the exterior extending longitudinally;
   (b) providing an extension wire having a proximal end and a distal end, the distal end having one or more non-circular keys, each key having dimensions complementary to the slot; and
   (c) inserting the key into the slot to releasably connect by frictional engagement the distal end of the extension wire and the proximal end of the guidewire.

14. A method used in angioplasty for connecting an extension wire to a guidewire comprising the steps of:
   (a) providing a guidewire section having proximal and distal ends, the proximal end having one or more non-circular attachment slots, each slot being a recessed chamber open at the proximal end, exposed along the exterior extending longitudinally, with widening tapers at the proximal end of the slot to facilitate engagement with a key;
   (b) providing an extension wire having a proximal end and a distal end, the distal end having one or more non-circular keys, each key having dimensions complementary to the slot, with narrowing tapers at the distal end of the key to facilitate engagement with the slot; and
   (c) inserting the tapered key into the tapered slot to releasably connect by frictional engagement the distal end of the extension wire and the proximal end of the guidewire.

15. A guidewire extension assembly for angioplasty including a guidewire and an extension wire to facilitate exchanging a balloon dilatation catheter comprising:
   (a) a guidewire having a proximal end and a distal end;
   (b) an extension wire having a proximal end and a distal end;
   (c) a first connector member and a second connector member;
   (d) the first connector member being mated to one end of the guidewire or extension wire and comprising an elongated chamber with a recess extending from the interior of the first connector member and exposed longitudinally along the exterior of the first connector member; and
   (e) the second connector member being mated to one end of either the guidewire or the extension wire, the second connector member comprising a finger like component extending longitudinally along the exterior of the second connector member, the second connector being dimensioned complementary to the elongated chamber of the first connector member such that when the first connector member and the second connector member are joined, at least one elongated chamber and one finger like component fit together and the combination of first and second connector members form a complete circle.

16. A guidewire extension assembly for angioplasty including a guidewire and an extension wire to facilitate exchanging a balloon dilatation catheter comprising:

(a) a guidewire having a proximal end and a distal end;

(b) an extension wire having a proximal end, a distal end and the distal end having a radius;

(c) the distal end of the extension wire having a key, the key having a proximal end and a distal end, the key having a length between 0.050 to 0.500 inches from the proximal end to the distal end, the proximal end of the key being contiguous with the distal end of the guidewire, the key having a lower surface parallel to the horizontal axis, the key having a curved upper surface, the curved upper surface having a radius the same as the radius of the extension wire, the lower surface and upper surface being connected together by two straight side surfaces, the lower surface, upper surface and side surfaces defining an outer surface of the key, the angle between the lower surface and the side surface being less than 90 degrees and the angle between the curved upper surface and the side surface being greater than 90 degrees, the width of the curved upper surface and width of the lower surface being between 0.0035 and 0.0070 inches, the height between the curved upper surface and the lower surface being between 0.0035 and 0.0070 inches, the side surfaces at the distal end of the key having tapers that narrow distally to facilitate engagement with the slot;

(d) the proximal end of the guidewire defining a longitudinally oriented slot, the slot having a open proximal end, a closed distal end, a lower surface and two side surfaces defining an inner surface, the inner surface of the slot being dimensioned to be complimentary to the outer surface of the key and the slot slidably fitting the key with an interference or frictional fit such that the key when inserted in the slot is held in place by frictional engagement to connect the distal end of the extension wire to the proximal end of the guidewire providing a smooth, continuous outer diameter between the guidewire and extension wire.

17. A guidewire extension assembly for angioplasty including a guidewire and an extension wire to facilitate exchanging a balloon dilatation catheter comprising:

(a) a guidewire having a proximal end and a distal end;

(b) an extension wire having a proximal end, a distal end and the distal end having a radius;

(c) the distal end of the extension wire having an upper key and a lower key;

(d) the upper key having a proximal end and a distal end, the upper key having a length between 0.050 to 0.500 inches from the proximal end to the distal end, the proximal end of the upper key being contiguous with the distal end of the guidewire, the upper key having a lower surface parallel to the horizontal axis and a curved upper surface, the curved upper surface having a radius the same as the radius of the extension wire, the lower surface and upper surface being connected together by two straight side surfaces, the lower surface and side surfaces defining an outer surface of the upper key, the angle between the lower surface and the side surface being less than 90 degrees and the angle between the curved upper surface and the side surface being greater than 90 degrees, the width of the curved upper surface and width of the lower surface being between 0.0035 and 0.0070 inches, the height between the curved upper surface and the lower surface being between 0.0035 and 0.0070 inches, the side surfaces at the distal end of the upper key having tapers that narrow distally to facilitate engagement with the slot;

(e) the lower key being dimensioned as the horizontal axial mirror image of the upper key;

(f) the proximal end of the guidewire defining a longitudinally oriented upper slot and longitudinally oriented lower slot;

(g) the upper slot having a open proximal end, a closed distal end, a lower surface and two side surfaces defining an inner surface, the inner surface of the upper slot being dimensioned to be complimentary to the outer surface of the upper key and slidably fit the upper key with an interference or frictional fit; and (h) the lower slot being dimensioned as the horizontal mirror image of the upper slot, the lower slot slidably fitting the lower key with an interference or frictional fit such that the upper key when inserted in the upper slot and the lower key when inserted in the lower slot are held in place by frictional engagement to connect the distal end of the extension wire to the proximal end of the guidewire providing a smooth, continuous outer diameter between the guidewire and extension wire.

18. A guidewire extension assembly for angioplasty including a guidewire and an extension wire to facilitate exchanging a balloon dilatation catheter comprising:

(a) a guidewire having a proximal end and a distal end;

(b) an extension wire having a proximal end, a distal end and the distal end having a radius;

(c) the distal end of the extension wire having an upper key and a lower key;

(d) the upper key having a proximal end and a distal end, the upper key having a length between 0.050 to 0.500 inches from the proximal end to the distal end, the proximal end of the upper key being contiguous with the distal end of the guidewire, the upper key having a first surface and a second surface, the first and second surfaces intersecting 90 degrees at the longitudinal axis of the extension wire and forming a "v"shape defining an outer surface of the upper key, a curved third surface connecting the first surface to the second surface at the radius of the extension wire, the third curved surface having a radius the same as the radius of the extension wire, the first surface and second surface at the distal end of the upper key having tapers that narrow distally to facilitate engagement with the slot;

(e) the lower key is dimensioned as the axial mirror image of the upper key;

(f) the proximal end of the guidewire defining a longitudinally oriented upper slot and a longitudinally oriented lower slot;

(g) the upper slot having an open proximal end, a closed distal end and a first surface and a second surface defining an inner surface, the inner surface of the upper slot being dimensioned to be complimentary to the outer surface of the upper key and slidably fit the upper key with an interference or frictional fit; and (h) the lower slot being dimensioned as the horizontal mirror image of the upper slot and slidably fitting the lower key with an interference or frictional fit such that the upper key when inserted in the upper slot and the lower key when inserted in the lower slot are held in place by frictional engagement to connect the distal end of the extension wire to the proximal end of the guidewire providing a smooth, continuous outer diameter between the guidewire and extension wire.

19. A guidewire extension assembly for angioplasty including a guidewire and an extension wire to facilitate exchanging a balloon dilatation catheter comprising:

(a) a guidewire having a proximal end and a distal end;

(b) an extension wire having a proximal end, a distal end and the distal end having a radius;

(c) the distal end of the extension wire having a upper key and a lower key;

(d) the upper key having a proximal end and a distal end, the upper key having a length between 0.050 to 0.500 inches from the proximal end to the distal end, the proximal end of the upper key being contiguous with the distal end of the guidewire, the upper key having a first surface and a second surface, the first and second surfaces intersecting 90 degrees at the longitudinal axis of the extension wire and forming a "v" shape defining an outer surface of the upper key, a curved third surface connecting the first surface to the second surface at the radius of the extension wire, the third curved surface having a radius the same as the radius of the extension wire, the first surface and second surface at the distal end of the upper key having tapers that narrow distally to facilitate engagement with the slot;

(e) the lower key having a length between 0.050 and 0.500 inches from the proximal end to the distal end, the key having a first surface parallel to the horizontal axis with a first edge and a second edge defining an outer surface, a curved second surface having the same radius as the extension wire with a first edge and a second edge, the first edge of the first surface being connected to the first edge of the second surface and the second edge of the first surface being connected to the second edge of the second surface;

(f) the proximal end of the guidewire defining a longitudinally oriented upper slot and longitudinally oriented lower slot;

(g) the upper slot having an open proximal end, a closed distal end and a first surface and a second surface defining an inner surface, the inner surface of the upper slot being dimensioned to be complimentary to the outer surface of the upper key and slidably fitting the upper key with an interference or frictional fit; and (h) the lower slot having an open proximal end, a closed distal end and a horizontal surface defining an inner surface, the inner surface of the lower slot being dimensioned to be complimentary to the outer surface of the lower key and slidably fitting the lower key with an interference or frictional fit such that the upper key when inserted in the upper slot and the lower key when inserted in the lower slot are held in place by frictional engagement to connect the distal end of the extension wire to the proximal end of the guidewire providing a smooth, continuous outer diameter between the guidewire and extension wire.

* * * * *